United States Patent
Rechberger et al.

(10) Patent No.: US 10,119,895 B2
(45) Date of Patent: Nov. 6, 2018

(54) METHOD, CIRCUIT AND FLEXURAL RESONATOR FOR MEASURING THE DENSITY OF FLUIDS

(71) Applicant: ANTON PAAR GMBH, Graz-Strassgang (AT)

(72) Inventors: Andreas Rechberger, Graz (AT); Robert Amsuess, Graz (AT)

(73) Assignee: Anton Paar GmbH, Graz-Strassgang (AT)

( * ) Notice: Subject to any disclaimer, the term of this patent is extended or adjusted under 35 U.S.C. 154(b) by 332 days.

(21) Appl. No.: 14/887,811

(22) Filed: Oct. 20, 2015

(65) Prior Publication Data
US 2016/0109347 A1    Apr. 21, 2016

(30) Foreign Application Priority Data
Oct. 20, 2014 (AT) .................................. 777/2014

(51) Int. Cl.
*G01N 9/00* (2006.01)
(52) U.S. Cl.
CPC .................................. *G01N 9/002* (2013.01)

(58) Field of Classification Search
None
See application file for complete search history.

(56) References Cited

U.S. PATENT DOCUMENTS

| | | | |
|---|---|---|---|
| 4,132,110 A * | 1/1979 | Muramoto | G01N 9/002 73/32 A |
| 7,735,353 B2 * | 6/2010 | Wagner | G01N 9/002 73/24.05 |
| 2004/0255648 A1 * | 12/2004 | Sparks | G01F 1/8404 73/54.41 |

\* cited by examiner

*Primary Examiner* — Paul West
*Assistant Examiner* — Mark S Shabman
(74) *Attorney, Agent, or Firm* — Laurence A. Greenberg; Werner H. Stemer; Ralph E. Locher

(57) ABSTRACT

A method for determining a density of a fluid medium with a flexural oscillator whose oscillator tube is filled with the measurement fluid. Accordingly, reference is made to a period of oscillation of a free and damped oscillating flexural resonator for density determination. For this purpose, the excitation of the excitation amplifier is interrupted alternately by a switch and then switched back into the oscillating circuit. The period of the damped oscillation, together with the amplitude and/or phase, is used for the output of a viscosity-corrected density.

8 Claims, 4 Drawing Sheets

METHOD, CIRCUIT AND FLEXURAL RESONATOR FOR MEASURING THE DENSITY OF FLUIDS

CROSS-REFERENCE TO RELATED APPLICATION

This application claims the priority, under 35 U.S.C. § 119, of Austrian application A 777/2014, filed Oct. 20, 2014; the prior application is herewith incorporated by reference in its entirety.

BACKGROUND OF THE INVENTION

Field of the Invention

The invention relates to a method for determining a density from a period of a flexural resonator determined from a period of a resonating oscillation mode, wherein the period is determined from a freely damped oscillating flexural oscillator, and is changed periodically between a forced undamped oscillation and a free oscillation with decreasing amplitude of the oscillation. The arrangement for performing the method, or a flexural resonator according to the invention, contains, in addition to the excitation circuit, measures for measuring the frequency and amplitude, and a periodically-switching interrupter which interrupts the excitation circuit for the measurement.

The measurement of the density of fluid media with a flexural resonator is based on the fact that the oscillation of a hollow body filled with a sample to be examined, is dependent on the filling of the oscillation tube of the oscillator, i.e. on the mass or, when the volume is constant, on the density of the filled medium.

A measuring cell contains the oscillatable structure, namely a hollow U-shaped glass or metal tube body. This is excited to oscillate by electronic measures. The two legs of the U-shaped tube form the spring elements of the oscillator. The natural frequency of the U-shaped tube oscillator is influenced only by that portion of the sample that is actually participating in the oscillation. This volume V participating in the oscillation is bounded by the stationary nodal points at the clamping points of the oscillator tube. If the oscillator tube is filled with the sample at least up to these clamping points and the same precisely-defined volume V always participates in the oscillation, then the mass of the sample can therefore be taken to be proportional to its density. Overfilling of the oscillator beyond the clamping points is irrelevant for the measurement. For this reason, the density of fluids can also be measured with the oscillator when the fluid is flowing through the oscillator.

The density of the fluids thus determines the specific frequencies at which the U-shaped tube oscillates. If one uses precision glass or metal tubes, then their properties vary depending on the density and viscosity of the liquid. The resonant frequencies are evaluated by appropriate excitation and pick-up of the oscillations and the density of the filled fluid sample is determined from the period. The oscillator is calibrated with fluids of known density thus enabling the measurements to be evaluated.

For the period P and the density $\rho$, then generally:

i)

$$\rho = P^2 \frac{R}{4\pi^2 V} - \frac{m}{V} = AP^2 - B.$$

Such density oscillators or flexural resonators have long been known and are produced in many different embodiments with respect to excitation and pick-up of the oscillations. The various means for excitation and pick-up of the resulting free oscillations can, for example, be effected by solenoid coils and magnets, piezoelectric elements, capacitive sensing etc. These means are preferably so applied to the oscillator that they do not lie at the nodal points of the natural oscillation to be examined.

In order to obtain higher accuracy results for these measurements, the flexural resonator must be configured so that it has the lowest possible damping as well as a high quality factor.

The high quality factor of the oscillator occurs in a narrow bandwidth of resonant frequencies. Thus, it is not practical to excite the natural frequencies with non-directional excitation (e.g. noise) or individual impulses.

The excitation is carried out by use of periodic signals, for example, rectangular pulses or sinusoidal waves. This can be done via a standard control loop or phase-shifted feedback.

The maximum amplitude and thus the natural oscillation of the frequency oscillator are regulated, for example, in a control loop by the pick-up signal. The oscillator is excited to forced oscillation at its resonant frequency, while the density of the medium filled in the frequency oscillator is determined from the determination of the period of this oscillation.

The output signal of the pick-up means the oscillation is phase shifted by 90 degrees in the mechanical system via a feedback loop, then amplified and this periodic signal is used for excitation of the oscillator. This causes the flexural resonator to oscillate in a forced oscillation.

FIG. 1 shows a schematic diagram of a known excitation amplifier.

The flexural resonator 1 is clamped in a holding device 2. Excitation is effected here, for example, by a piezoelectric element 3 near the clamping point of the first leg of the oscillator, wherein a pick-up means is affected by a second piezoelectric element 4 on the second leg of the oscillator. The combination of a phase shifter 6 and an amplifier 7 form the simple excitation amplifier. The output of the pick-up means is amplified and phase-shifted by 90°, and then fed to the means for oscillation excitation. The oscillator can be "oscillated up" to a state of resonant oscillation by such an excitation amplifier. The period or frequency of oscillation is measured by the frequency meter 5 and fed to an evaluation unit for the density determination.

Known flexural oscillators are operated according to this principle with analogue and digital excitation amplifiers, while the density of the fluid medium to be examined is determined in a known manner from the frequency or period of the oscillator.

The actual density of the fluid media is strongly dependent on the temperature. As a rule, this is at least measured and/or the entire oscillator or the sample is heated to a specific measuring temperature by appropriate device (e.g. Peltier elements).

If one determines the density with the flexural resonator, then due to the different behavior of samples of the same density of different viscosities in the resonator, the viscosity of the sample has a relatively large influence on the measurement result and must also be taken into account. In addition to its influence on the determined density, the viscosity expresses itself especially through its influence on the damping or quality factor of the oscillator.

Different methods for correcting the viscosity-dependent density values are known, wherein a representative parameter for this damping is evaluated and the density measurement corrected. This is usually based on additional excited oscillations in the range of the so-called harmonics by considering the phase relationship for excitation. Alternatively, for example, the use of a superimposed control loop which varies the amplitude of the excitation signal in order to obtain constant oscillation amplitude is known. The energy introduced via the excitation signal thus corresponds to the damping of the system and can be used for quality factor determination.

However, the quality factor measurement may also be effected by measuring the decreasing amplitude with periodic uncoupling of the exciter as this is theoretically the best solution for determining the quality factor. Thus, any inaccuracies in the excitation (e.g. non-linearity's and/or phase distortions of filters, etc.) are avoided.

However, in the case of high quality factor resonators, these have the disadvantage of long measurement times, always only represent a single measurement, and also influence the period of the forced oscillation. Preferably, therefore, no interruptions of the oscillator are carried out after the excitation.

In all these known arrangements, the period of the forced fundamental oscillation is generally used for the evaluation for the density measurement.

The disadvantages of such arrangements are, for example, in the amplitude modulation, wherein the resonance frequency is not precisely measured, because non-linear distortions (electronics, IIR filters), as well as time delays (time quantization) of the analogue to digital converter (ADC) and/or digital to analogue converter (DAC) signals, also play a role.

In addition, the high quality factor and thus the resulting low bandwidth of the oscillator require very small modulation frequencies of the order of $1/1000 \ldots 1/2000$ of the natural frequency.

For example, for resonant frequencies in the range of 300 Hz (glass oscillator) to 5000 Hz (metal), and quality factor values of 10 . . . 5000 (glass) and 10 . . . 14,000 (metal), modulation frequency in the range of $1/3 \ldots 1/10$ Hz is used. This results in 3 . . . 10 sec for the period run.

The lower the modulation frequency, the longer is the decay measurement of the quality factor, because, in general, a new measured value is available once per period of the modulation frequency. Thus, every 3 to 10 sec according to the medium. In addition, additional averaging is necessary as a function of the required accuracy.

SUMMARY OF THE INVENTION

According to the invention, it is now proposed that the advantages of the determination of the period by means of forced oscillation (continuous measurement methods, parallel phase control) are combined with the advantages of the measurement of the decay behavior for the measurement of the quality factor independently of the excitation, in order to directly examine both the quality factor and the period of the oscillator excitation by use of continuous decay measurement and to evaluate them in terms of the viscosity-corrected density.

There is no longer the disadvantage of only one-off measurement by periodically measuring the decay behavior. Since the entire determination of the density and viscosity correction results from the decay behavior, the influence of the period or phase measurement from the renewed oscillation upwards of the excitation amplifier circuit is no longer a problem.

In addition, higher accuracies can be achieved here with lower quality factors of the oscillator.

Other features which are considered as characteristic for the invention are set forth in the appended claims.

Although the invention is illustrated and described herein as embodied in a method, a circuit and a flexural resonator for measuring the density of fluids it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 2:
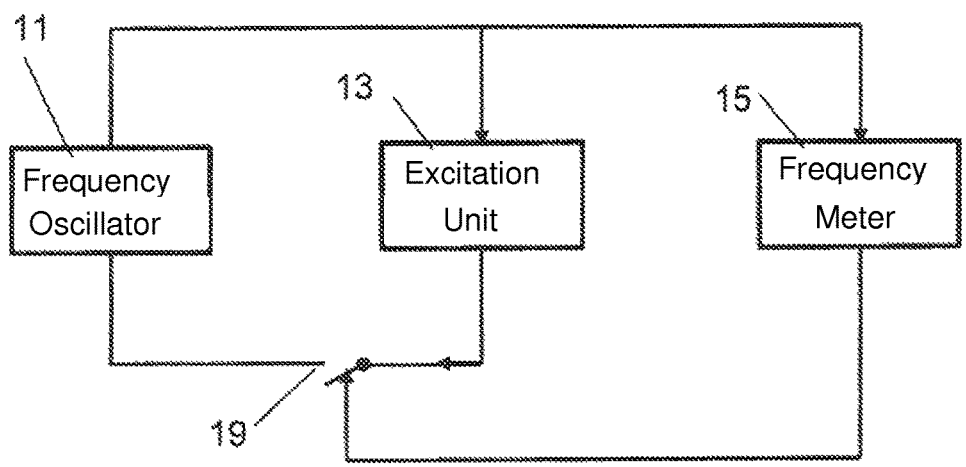
FIG. 2 is a block diagram of a circuit according to the invention.

Referring now to the figures of the drawings in detail and first, particularly to FIG. 2 thereof, there is shown a block diagram of the invention. An excitation or excitation unit 13 shifts a resonator 11 into resonance. This can be done via a standard control loop or a phase-shifted feedback, for example, −90° resonance condition of the oscillator. This allows the implementation of a quasi "control-less" exciter, because the −90° phase rotation represents a pure signal transformation, in contrast to a controlled oscillator based on a phase comparison (output/input) at the −90° point. The period or frequency of oscillation is measured by the frequency meter 15 and supplied to an evaluation unit for density determination.

According to the invention it is now proposed that both the period and the amplitude of forced resonant oscillation can be determined only after the decoupling of the exciter, i.e. only the decaying oscillation of the flexural resonator is examined. The excitation thus has no influence on the measurement itself, and does not require any information about the current measurement cycle. A switch or interrupter 19 periodically interrupts the excitation of the oscillator to this end. The excitation circuit is interrupted for a period of time t1 via the switch 19, and a decay behavior of the oscillator 11 is examined. Then the switch is closed again and the excitation circuit 13 again forces the frequency oscillator 11 from its free damped oscillation into forced undamped oscillation. Preferably, the excitation circuit is closed until the forced resonant oscillation of the oscillator oscillates at its maximum amplitude, or the maximum amplitude has been reached.

Figure 3:
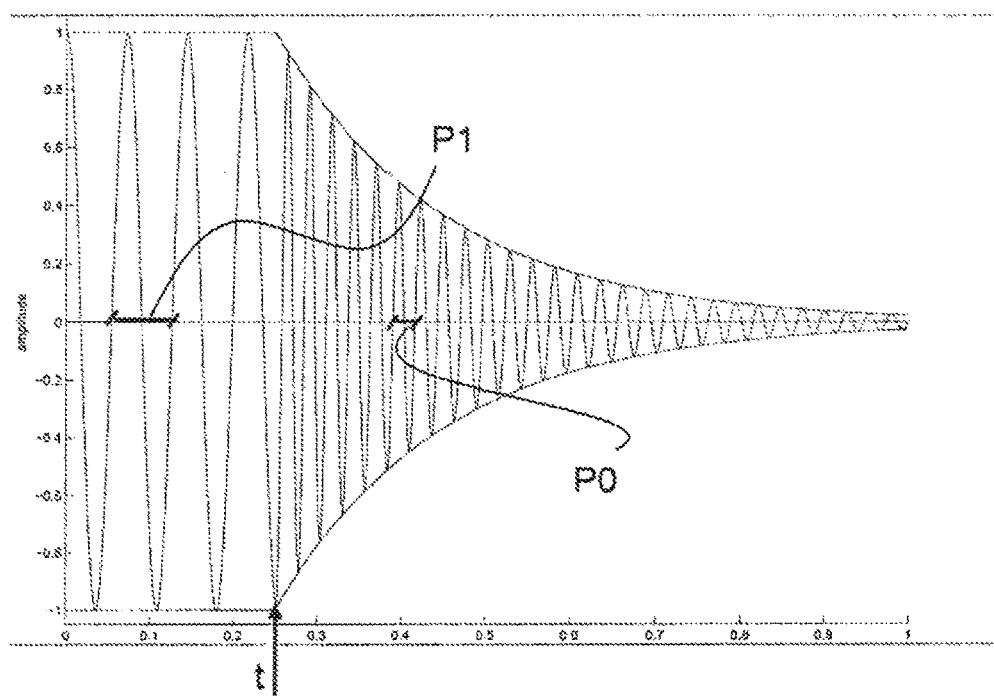
FIG. 3 is a graph showing a decay of an oscillator.

FIG. 3 shows such a decay of the oscillator. Following the decoupling of the excitation circuit at the time t, the amplitude of the oscillation decays faster or slower over time as a function of the quality factor of the oscillator. The actual resonant frequency and the period P0 is slightly different here from the forced oscillation (period P1), because the non-linearities and time errors of the excitation circuit are omitted and the free oscillator oscillates at its resonant frequency. The image shows a highly exaggerated difference between the periods as an illustration.

Figure 4:
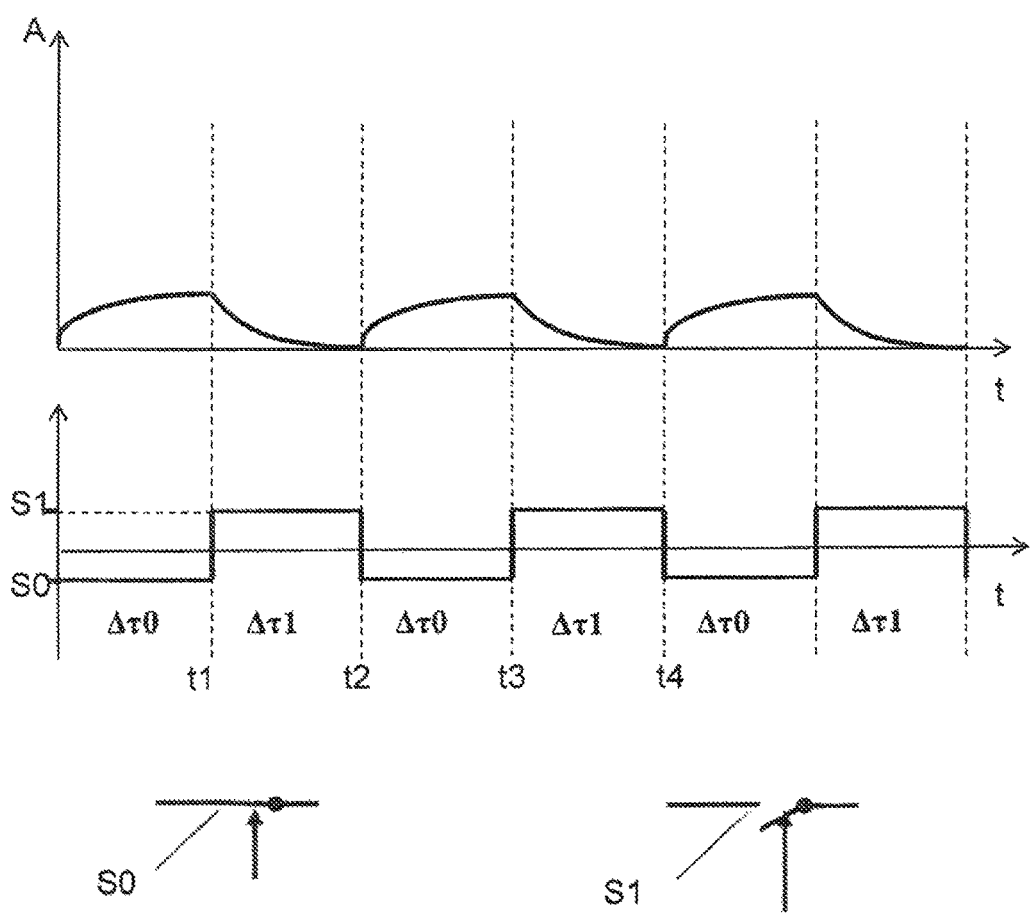
FIG. 4 is a time-line graph showing an image of a periodic switching on and off of the exciter (switch in position S0—wherein the oscillator oscillates upwards in the resonance) with corresponding signals for an amplitude A as a function of the time.

FIG. 4 shows the image of the periodic switching on and off of the exciter (switch in position S0—wherein the oscillator oscillates upwards in the resonance) with the corresponding signals for the amplitude A as a function of the time.

The amplitude increases with the transient response. Upon excitation, the amplitude curve follows a function of the type.

$$1 - e^{-\frac{t}{\tau}}$$

At time t1, the switch is opened (switch in position S1), the oscillator oscillates damped here, the amplitude shows the decay behavior, while, in this period, the oscillation is evaluated with respect to the frequency and amplitude. At time t2, the switch is closed again, the oscillator oscillates upwards again and the forced oscillation is excited again. This procedure is repeated periodically (t3, t4, . . . )

The control of this period can, for example, be carried out respectively via the signal amplitude of the oscillation, both in oscillation as well as in decay, upon reaching a certain amplitude value, and the period for switching of the switch 19 can be derived from this. Alternatively, a not strictly periodic switching on and off of the excitation can also be made directly. The amplitude does not have to fall to 0 (complete decay) but it can already be coupled again earlier.

This makes it possible to measure the period or frequency of the oscillator during the decay process, while eliminating all implementation-dependent deviations of the excitation, because this is not applied to the oscillator during the decay measurement.

Furthermore, the measurement of the frequency of the oscillator with a frequency comparison measurement can be performed, and is very accurate (phase drift of the beat amplitude).

Since the excitation is measurement invariable, one can rapidly switch between decay and excitation mode (several times per second).

In an advantageous embodiment of the invention, it may be provided that the decay process is interrupted after a predetermined time interval or on reaching a predetermined amplitude value, and from the obtained amplitude values the quality factor and/or the width of the decay window is calculated by extrapolation, or the time interval for the decay is held constant or selected.

Therefore, the decay process need not be complete, because the quality factor can be calculated by extrapolation of the amplitude values even in the case of a small amplitude drop. Thus, the decay window may have a constant with independent of the filling of the oscillator. The accuracy of the quality factor measurement thus increases with decreasing quality factor, as the difference in amplitude within the constant decay window increases, and thus the difference with respect to a constant noise.

Preferably, the interval for switching on and off is determined respectively for each oscillator. Depending on the quality factor and amplitude of the resonance oscillation examined, the duration $\Delta\tau0:\Delta\tau1$ of the time intervals for the excitation through the decay is in the ratio 1:1 to 1:3. This is also influenced by the available "excitation energy", i.e. the voltage at the piezoelectric crystal, the current through the coil, because shorter oscillation times can be obtained as a result of the higher energy introduced.

Preferably, it is provided that the interrupter or switch 19 which interrupts the excitation amplification, is only applied at the output of the excitation amplifier circuit. Thus, the oscillating circuit of the excitation amplification may be held in phase with the period of the flexural oscillator in the event of an interruption, while, upon switching on again, the excitation amplification can again rapidly achieve the initial amplitude through in-phase excitation. The excitation amplifier may be located before or after the DAC.

The decaying oscillation or its decaying sine is analyzed according to the frequency and amplitude of these two values, wherein the density of the medium located in the oscillator is determined in an evaluation and display unit. Viscosity corrections and filling error detection can be carried out, for example, through further processing of the signal. The calibration curves and calibration constants required for this are stored in the control and evaluation unit after calibration adjustment to standards of known density and viscosity.

The measurement of the decay curves can be carried over optionally long periods, for example, the measurement is carried out in the case of a metal oscillator with 4 . . . 5 kHz resonant frequency (corresponding to a period of about 200 . . . 250 µs), in the case of an air-filled oscillator with a decay time $\Delta\tau1$ of approx 65 msec.

Generally decay periods are preferably shorter than 1 sec in order to be able to perform the measurements sufficiently quickly. Long measurement times are required in the case of high quality factors, because the amplitude of the oscillator only changes slowly due to the low damping. The selection of the duration of the decay measurement is also performed as a function of the accuracy, the electronic components and the computing power.

The determination of frequency and amplitude can, for example, be effected by a Fourier analysis, while the frequency determination can, for example, be effected directly by mixing a local oscillator with the measurement signal or determination of the zero crossings of the measurement signal. The amplitude can, for example, be measured directly and instantaneously independently of the frequency, by sliding maximums etc. In the case of direct measurement of the amplitude, each individual ADC sample, i.e. each measured value from the ADC, is thus assigned its own amplitude value.

Figure 5:
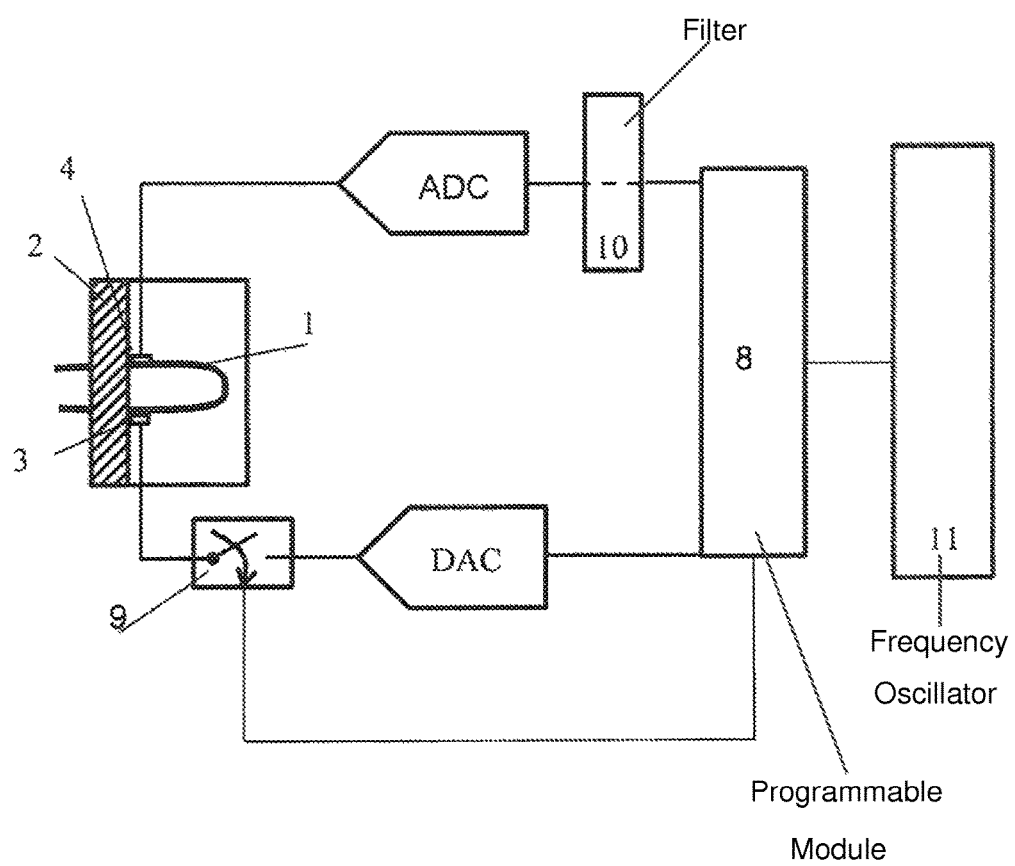
FIG. 5 is a block diagram of a circuit of a flexural oscillator according to the invention.

FIG. 5 shows an embodiment of the circuit construction of a flexural oscillator according to the invention. A switch 9 is closed in the initial state. The flexural oscillator is advantageously equipped with a unit for excitation and a unit for pick-up in the form of two piezoelectric elements for excitation 3 and pick-up 4. The excitation and pick-up is via analogue voltage signals. The signal pick-up unit 4 is digitized through an analogue-to-digital converter (ADC) and passed into a programmable digital module 8, in which the central control and regulating tasks are taken over.

The central module 8 of a digital implementation has to ensure the fastest possible signal processing; this can, for example, be implemented by a p-controller or digital signal processor (DSP). Preferably a field programmable gate array (FPGA) is used in view of the achievable control speed.

Figure 1:
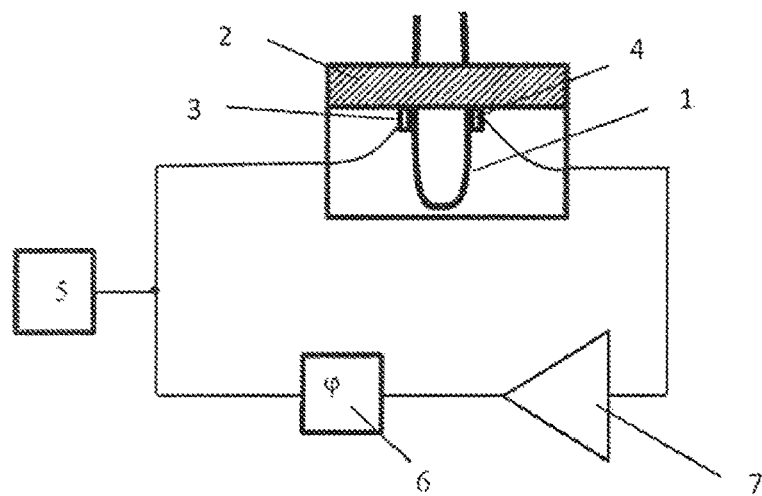
FIG. 1 is a schematic diagram of an excitation amplifier according to the prior art.

The excitation amplifier circuit described in principle in FIG. 1 is implemented by means of this module and a further digital-to-analogue processor, wherein the control signal drives the excitation unit 3. The amplified output signal is phase shifted by 90° with respect to the input signal and excites the oscillator into forced oscillation.

Alternatively, instead of the piezoelectric elements, any electrical components may be used for excitation and pick-up of the oscillation, for example, a combination of current-carrying coils and permanent magnets. The excitation and pick-up may also take place in other parts of the oscillator, for example, laterally to the legs. The coil currents of the coils can be used as the output and control signals.

A central component of the arrangement is now an electronic switch 9, which is also controlled by the central module 8, i.e. it is periodically opened and closed.

The frequency and period determination of the oscillation of the flexural resonator is effected by comparison with the signal of a local oscillator or directly by mixing a local oscillator with the measurement signal and comparing the oscillation signal of a local oscillator with the measurement signal.

A frequency comparison of the input signal $\omega 1$ is carried out, i.e. the pick-up signal from the piezoelectric element 4 that provides the period of the flexural resonator, with the signal of a local oscillator $\omega 2$.

By multiplying the two signals, then:

$$\cos \omega 1 * \cos \omega 2 \sim \cos(\omega 1 - \omega 2) + \cos(\omega 1 + \omega 2).$$

The local oscillator is so controlled that the two frequencies are equally large, and thus the first term refers to a pure amplitude (DC signal), while the second term can be simply filtered due to the large difference of the signals. The harmonic for a 4 kHz oscillator would be $\omega 1 = \omega 2$ at 8 kHz here.

In order to increase the accuracy and/or to determine the viscosity correction with two different resonant oscillations, it may be desired to excite the oscillator not only into a resonant mode, but simultaneously into a second resonant mode, e.g. the first harmonic, with which the excitation amplifier is excited. In the case of a digital excitation amplifier, this can take place simultaneously by superimposing the respective excitation signals.

An additional filter 10 can be provided to evaluate these two oscillations in order to again separate the response signal from the frequency oscillator into the two frequencies.

The frequency-independent and instantaneous amplitude measurement assigns each ADC sample with its own amplitude value, so that it is not necessary to carry out the measurement over an entire period of oscillation.

In this way, the local oscillator is implemented as a complex rotor instead of the usual real sine representation $(y=\sin(\omega t))$:

$$y=\exp(j\omega t)=\cos(\omega t)+j\sin(\omega t).$$

The signal amplitude is determined by means of transformation of the Cartesian representation of the ADC signal in polar coordinates:

$$y=A*e^{(jP)}.$$

Furthermore, an amplitude-independent determination of the current phase is possible:

Since a corresponding complex data point can be assigned for each individual input sample, instantaneous determination of the phase position of the oscillator is also possible. The period or frequency can be calculated by simple differentiation of the phase. This measurement is thus independent of the amplitude measurement or the actual oscillator frequency.

According to the invention, an inventive method is further provided for measuring the density from the period of a resonant oscillation mode of a flexural oscillator, wherein the oscillator is shifted into a resonant undamped oscillation in an excitation amplifier circuit, wherein the method is characterized in that the oscillator is shifted into forced undamped oscillation during a time interval $\Delta t_1$ by an excitation amplifier, wherein the excitation of the forced oscillation is interrupted periodically, and wherein the oscillator then oscillates freely and damped as a function of its quality factor during a time interval $\Delta t_2$, wherein the period of the free damped oscillation is used for density determination, and the oscillator is excited again into undamped oscillation following the measurement.

A method for measuring the density of the above kind may be further characterized by a control and/or regulating circuit and that an interrupter is provided in the excitation circuit to excite the oscillator into the undamped oscillation, and which repeatedly switches at defined time intervals between the excitation circuit for the undamped oscillation of the flexural resonators and a flexural resonator without a specified excited damped oscillation, while the period of oscillation to determine the density is measured with an open field circuit.

Preferably, the interrupter or switch 9 which interrupts the excitation amplitude is mounted at the output of the excitation amplifier circuit. Thus, the oscillation circuit of the excitation amplitude may be held in phase with the period of the flexural resonator 1 in the event of an interruption and upon switching the excitation amplifier on again, wherein the original amplitude can rapidly reach the in-phase excitation again. In this case, the excitation amplifier may be located before or after the DAC.

It is advantageous, furthermore, if the interrupter is installed subsequent to the excitation amplifier in the excitation amplifier circuit and that the amplified output signal for the amplifier circuit is in phase with the flexural resonator. This ensures that the excitation amplifier circuit remains in phase with the oscillator. When the switch is closed again, the frequency of the forced oscillation does not have to be adjusted again, but will be "forced" to coincide with the proper phase relationship.

The invention claimed is:

1. A method for measuring a density of fluids from a period of a resonant oscillation mode of a flexural resonator, which further comprises:
    operating an oscillator in a resonant undamped oscillation with an excitation amplifier circuit;
    operating the oscillator in a forced undamped oscillation during a time interval $\Delta t_1$ via an excitation amplifier;
    periodically interrupting an excitation of the forced undamped oscillation for a time interval $\Delta t_2$, the oscillator is left free and allowed to oscillate damped as a function of its quality factor during the time interval $\Delta t_2$ of an interruption, in the time interval $\Delta t_2$, a period of a free damped oscillation is used for a density determination; and
    exciting the oscillator again into the resonant undamped oscillation after a measurement of the period of the free damped oscillation.

2. The method according to claim 1, which further comprises:

evaluating the free damped oscillation in terms of at least one parameter selected from the group consisting of phase and amplitude; and making a viscosity correction of a determined density value with the parameter.

3. The method according to claim 1, which further comprises determining a period of an oscillation frequency by carrying out a comparison with a local oscillator.

4. The method according to claim 2, which further comprises carrying out an amplitude determination directly by means of coordinate transformation of a measuring signal.

5. The method according to claim 1, which further comprises performing a periodic switching on and off of the excitation amplifier circuit for predetermined, fixed, equal length, time intervals and/or that the switching on and off of the excitation amplifier circuit is regulated by means of amplitude values of a damped oscillation and/or an undamped oscillation.

6. The method according to claim 5, wherein the time interval $\Delta t_1$ of the excitation amplification is in a fixed relationship to the time interval $\Delta t_2$ of a period measurement, wherein a ratio $\Delta t_1 : \Delta t_2$ lies in a range of between 1:1 to 1:3.

7. The method according to claim 1, wherein:
the excitation amplifier circuit remains closed until a forced resonant oscillation of the oscillator reaches its maximum amplitude; and/or
both a period and an amplitude of the forced undamped oscillation are determined after a decoupling of an exciter.

8. The method according to claim 1, wherein:
a decay is interrupted:
after a predetermined time interval; or
when a predetermined amplitude value is reached; and
the quality factor is calculated through extrapolation of obtained amplitude values; and/or
a width of a decay window is selected or held constant; or
the time interval selected for the decay is selected or held constant.

* * * * *